(12) United States Patent
Kirsch et al.

(10) Patent No.: US 6,565,579 B2
(45) Date of Patent: May 20, 2003

(54) METHOD AND DEVICE FOR URETHRAL-VESICLE ANASTOMOSIS

(75) Inventors: Wolff M. Kirsch, Redlands, CA (US); Yong Hua Zhu, Redlands, CA (US); Robert R. Torrey, Jr., Redlands, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 0 days.

(21) Appl. No.: 10/237,434

(22) Filed: Sep. 5, 2002

(65) Prior Publication Data

US 2003/0032968 A1 Feb. 13, 2003

Related U.S. Application Data

(63) Continuation of application No. 09/618,373, filed on Jul. 17, 2000, now Pat. No. 6,461,367.
(60) Provisional application No. 60/144,429, filed on Jul. 16, 1999.

(51) Int. Cl.[7] .............................................. A61B 17/03
(52) U.S. Cl. ...................................... 606/144; 606/139
(58) Field of Search ................................ 606/139, 142, 606/144, 148, 149, 153, 228; 227/179.1, 181.1

(56) References Cited

U.S. PATENT DOCUMENTS

| 4,848,367 | A | 7/1989 | Avant et al. |
| 5,047,039 | A | 9/1991 | Avant et al. |
| 5,344,059 | A | 9/1994 | Green et al. |
| 5,545,171 | A | 8/1996 | Sharkey et al. |
| 5,591,179 | A | 1/1997 | Edelstein |
| 5,713,889 | A | 2/1998 | Chang |
| 5,718,360 | A | 2/1998 | Green et al. |
| 6,053,390 | A | 4/2000 | Green et al. |
| 6,080,167 | A | 6/2000 | Lyell |
| 6,461,367 | B1 * | 10/2002 | Kirsch et al. ............... 606/144 |

FOREIGN PATENT DOCUMENTS

| WO | WO 99/47050 | 9/1999 |
| WO | WO 99/55238 | 11/1999 |

* cited by examiner

Primary Examiner—Danny Worrell
(74) Attorney, Agent, or Firm—Knobbe, Martens, Olson & Bear LLP

(57) ABSTRACT

An improved device and method are provided for securing the urethra to the bladder in surgery.

A trocar is provided for insertion into the urethra. The trocar is removably secured to the urethra for advancement of the proximal end toward the bladder. A sheath is inserted and secured to the bladder in order to assist in the advance of the bladder toward the urethra. The improved system permits medical personnel to clamp the urethra and bladder without the need for insertion of time consuming and laborious sutures. A method of securing the urethra and bladder using the disclosed apparatus is also provided.

4 Claims, 15 Drawing Sheets

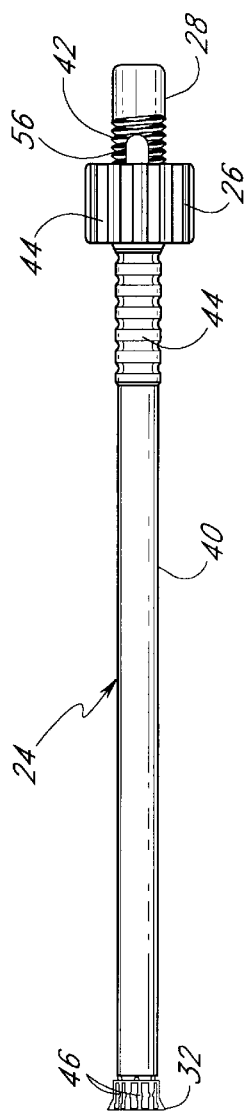
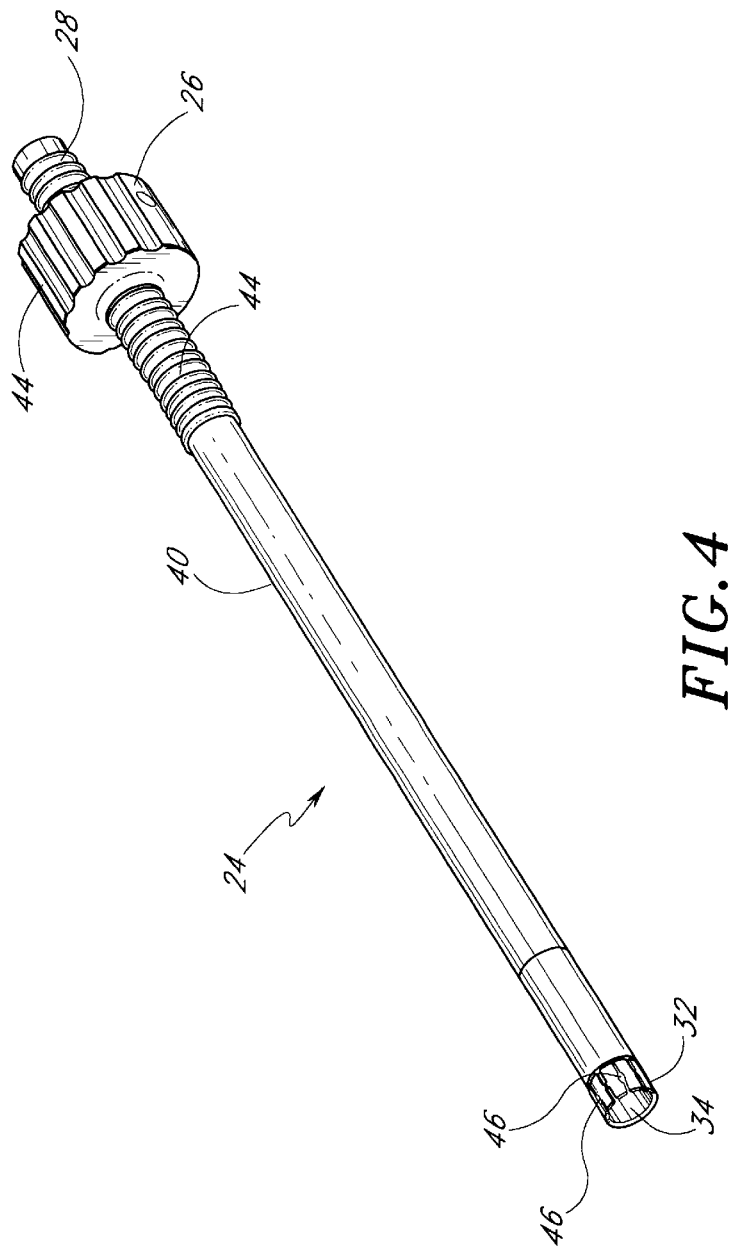
FIG.3
FIG.4

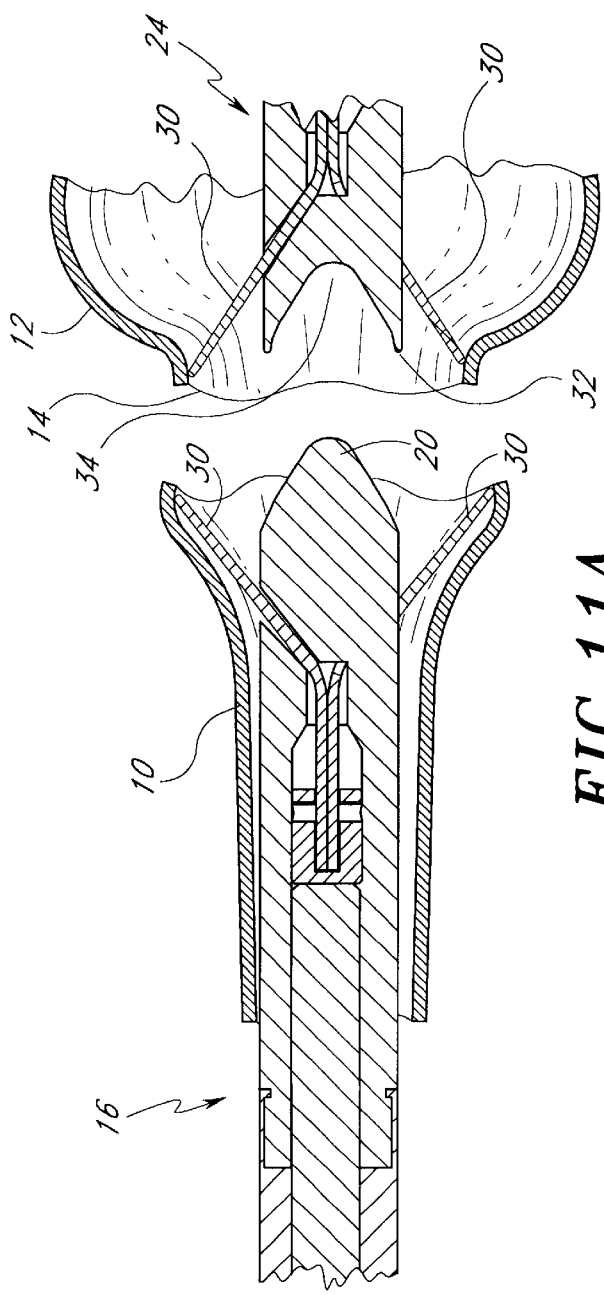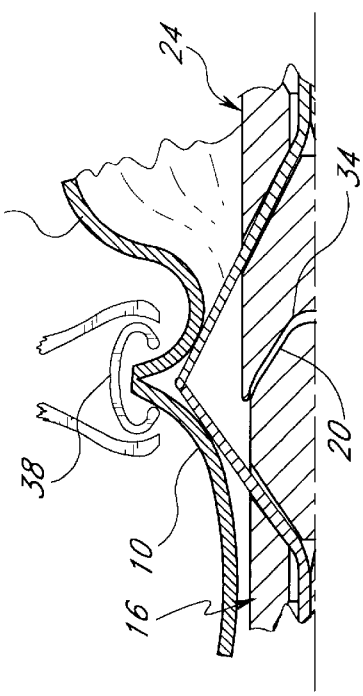
FIG. 11A
FIG. 11B

METHOD AND DEVICE FOR URETHRAL-VESICLE ANASTOMOSIS

RELATED APPLICATIONS

This application is a continuation of U.S. patent application Ser. No. 09/618,373, filed Jul. 17, 2000, now U.S. Pat. No. 6,461,367 titled METHOD AND DEVICE FOR URETHRAL-VESICLE ANASTOMOSIS, which application in turn claims the benefit of U.S. Provisional Application Ser. No. 60/144,429, filed Jul. 16, 1999, titled METHOD FOR URETHRAL-VESICLE ANASTOMOSIS. The entirety of each of the above-mentioned applications is hereby incorporated by reference herein.

BACKGROUND OF THE INVENTION

1. Field of the Invention

The present invention generally relates to the reconnection of the urethra and bladder after a radical retropubic prostatectomy. Specifically, the invention relates to a method and device for performing a urethral-vesicle anastomosis.

2. Description of the Related Art

In a radical retropubic prostatectomy, the surgeon removes all or most of the patient's prostate. Because the urethra travels through the prostate immediately before reaching the bladder, the upper part of the urethra is removed in the surgery. In order to restore proper urinary functions, the bladder and the urethra must be reconnected.

Heretofore, surgeons would execute painstaking suturing operations with tiny, fine needles to reconnect these anatomical bodies. It has been found that the use of sutures for this purpose has caused certain problems in recovery. These problems include necrosis of the sutured tissues, stricture of the urethra which impedes the flow of fluid through it, and a urethra-bladder connection which is not fluid-tight. In addition, when suturing the urethra to the bladder the surgeon often inadvertently pierces the nearby neurovascular bundle, which can cause incontinence or impotence.

The suturing process itself has also been found to be cumbersome, requiring the surgeon to grasp and stretch the bladder and urethra together before making the fine sutures.

With radical retropubic prostatectomies becoming more common, a quicker and simpler way to reconnect the bladder and the urethra is needed.

SUMMARY OF THE INVENTION

One aspect of the present invention is an improved method for the anastomosis of the urethra to the bladder following a prostatectomy.

A further aspect of the present invention is an anastomosis procedure that eliminates the use of sutures in the urethra-bladder junction.

A still further aspect of the present invention is an anastomosis procedure with an improved means of grasping the urethra and bladder, bringing them together and holding them for the connection process.

A method and device are provided for the anastomosis of the urethra and bladder after radical retropubic prostatectomy. The surgeon inserts a trocar into the urethra and secures the bladder to the trocar with an external ring, or, alternatively, with at least one prong associated with the trocar. The surgeon then inserts a sheath into the bladder and secures the bladder to the sheath with at least one prong. The trocar and the sheath are then advanced toward each other, and fit together in an end-to-end fashion. When the urethral tissue and the bladder tissue are in close proximity, the urethra and the bladder are reconnected using at least one clip. The urethra is secured to the bladder In accordance with one preferred embodiment, a method is provided for securing the urethra to the bladder of a patient. The method comprises the steps of inserting a first approximation device into the urethra, securing the urethra to the first approximation devices inserting a second approximation device into the bladder and securing the bladder to the second approximation device. The method further comprises the step of advancing the second approximation device toward the first approximation device so that a distal end of the urethra comes in close proximity to a distal end of the bladder. The final step of the method comprises securing the urethra to the bladder.

In accordance with yet another preferred embodiment, a method for securing the urethra to the bladder of a patient comprises the steps of inserting a first approximation device into the urethra, securing the urethra to the first approximation device, inserting a second approximation device into the bladder and securing the bladder to the second approximation device. The method further comprises advancing the first approximation device and the second approximation device toward one another so that a distal end of the urethra comes in close proximity to a distal end of the bladder. Finally, the urethra is secured to the bladder.

In accordance with still another preferred embodiment, there is provided a system for securing the urethra of a patient to the bladder of the patient. This system comprises a first approximation device adapted to be inserted into the urethra of the patient and a ring. The ring is suitable for placement on a exterior of the urethra for securing the urethra to the first approximation device. The system further comprises a second approximation device adapted to be inserted into the bladder. The second approximation device has at least one prong on a cannula of the second approximation device. The prong secures the second approximation device to the bladder. The system further comprises at least one clip. The clip is suitable to secure the urethra to the bladder once the urethra and bladder are within close proximity.

In accordance with still another preferred embodiment, there is provided a system for securing the urethra of a patient to the bladder of the patient. The system comprises of first approximation device that has a generally rigid cannula and at least one prong. The prong is moveable from a retracted position to an extended position on a exterior surface of the cannula to secure the urethra to the first approximation device. The system also comprises a second approximation device that has a generally rigid cannula and at least one prong. The prong is moveable from a retracted position to an extended position on an exterior surface of the cannula to secure the bladder to the second approximation device.

BRIEF DESCRIPTION OF THE DRAWINGS

FIG. 3 is a side elevation view of a sheath;

FIG. 4 is a perspective view of a sheath;

FIGS. 11A and 11B are cross-sectional views of the joining of the bladder and urethra tissues, employing another embodiment of the trocar and sheath;

DETAILED DESCRIPTION OF THE PREFERRED EMBODIMENT

Figure 1:
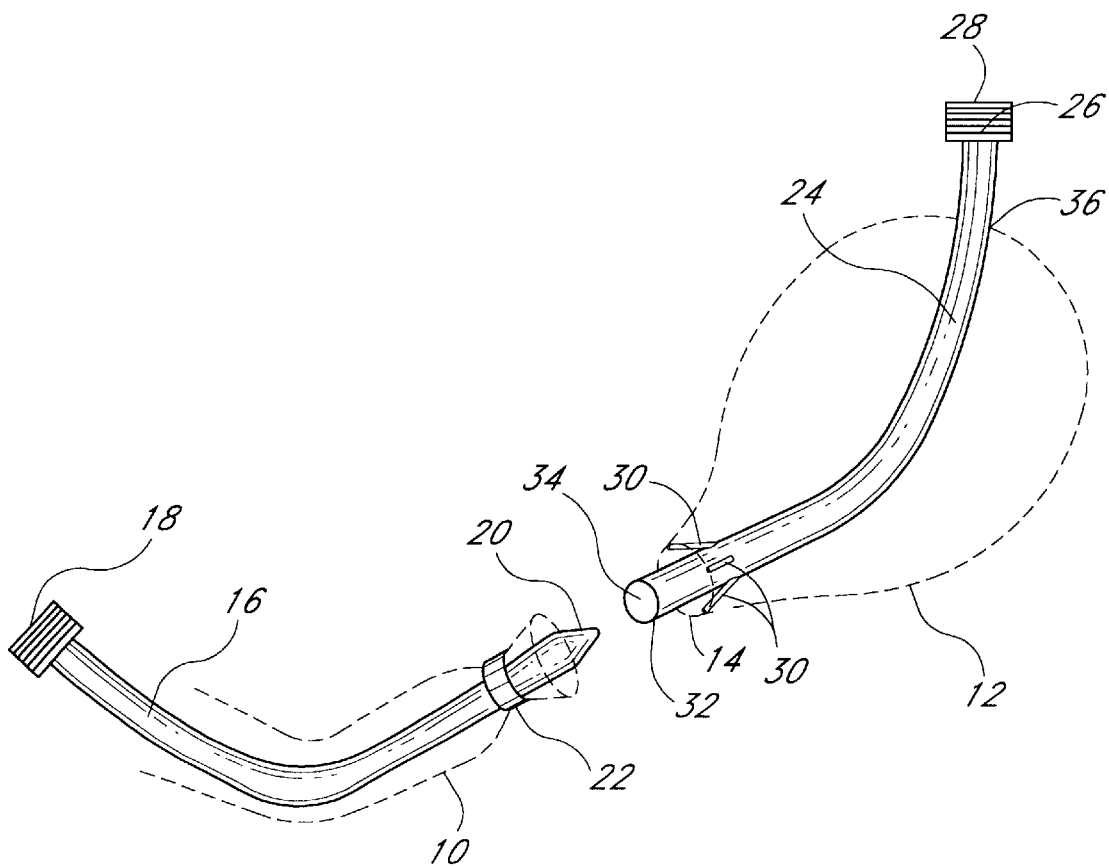
FIG. 1 is a schematic view of a trocar and sheath as used to join the bladder and urethra in accordance with the present invention.

FIG. 1 depicts, among other things, the relevant anatomical structures of a patient following a radical retropubic prostatectomy. The urethra 10 has been separated from the bladder 12 by virtue of the removal of the prostate (not shown). The urethra 10 must therefore be re-attached to the bladder 12 at the bladder outlet 14.

To rejoin the bladder and urethra, a urethra approximation trocar 16, comprising a proximal end 18 and a tapered distal end 20, may be inserted into the urethra 10 via the urethral outlet in a manner known to those skilled in the art. The trocar 16 is preferably constructed of a stiff plastic or metal to provide sufficient rigidity despite a cross-sectional area small enough to permit the trocar 16 to pass through the urethra. The trocar 16 is advanced within the lumen of the urethra 10 so that the tapered or rounded distal end 20 of the trocar 16 emerges from the urethral passage. The urethra 10 is then secured to the trocar 16 in a manner which will prevent the urethra 10 from sliding backwards, away from the tapered distal end 20 of the trocar 16, when the trocar is subsequently advanced toward the bladder 12. Preferably, this is accomplished by a removable external ring 22 placed around the urethra 10 near the distal end 20, securing the urethra 10 to the trocar 16. Another method to secure the urethra with respect to the trocar is by means of one or more everting prongs extendable from the outer surface of the trocar 16 near the distal end 20. (This is similar to the everting prongs 30 extendable from the sheath 24, the operation of which will be discussed in greater detail below.) The prongs evert the urethra tissue from the trocar shaft, pushing it out radially to facilitate attachment.

FIG. 1 also depicts a urethra approximation sheath 24 having an everting knob 26 on the proximal end 28 and multiple everting prongs 30 near the distal end 32. The distal end 32 also forms a cavity 34 which is sized so as to snugly receive the tapered end 20 of the trocar 16 (see FIG. 2). As with the trocar 16, the sheath 24 is preferably constructed of a stiff plastic or metal to provide sufficient rigidity despite a cross-sectional area small enough to permit the sheath 24 to pass through the bladder outlet 14.

To insert the sheath 24, the surgeon first makes an abdominal incision 36 to gain access to the bladder 12. The sheath 24, with everting prongs 30 in a retracted position, is inserted into the incision 36 and is advanced toward the bladder outlet 14 so that the distal end 32 of the sheath 24 emerges from the bladder outlet 14. By manipulation of the everting knob 26, the everting prongs 30 are extended from the sheath 24 and positioned inside the bladder 12 such that they engage the bladder tissue near the bladder outlet 14, securing the bladder 12 with respect to the sheath 24. The everting prongs 30 thus prevent the bladder 12 from sliding backward on the sheath 24, away from the distal end 32 of the sheath 24, when the sheath 24 is subsequently advanced toward the urethra 10. In addition, the everting prongs 30 pull the tissue of the bladder 12 both longitudinally and radially to facilitate the eventual application of one or more clips to the junction of the bladder and urethra (see FIG. 2).

Figure 2:
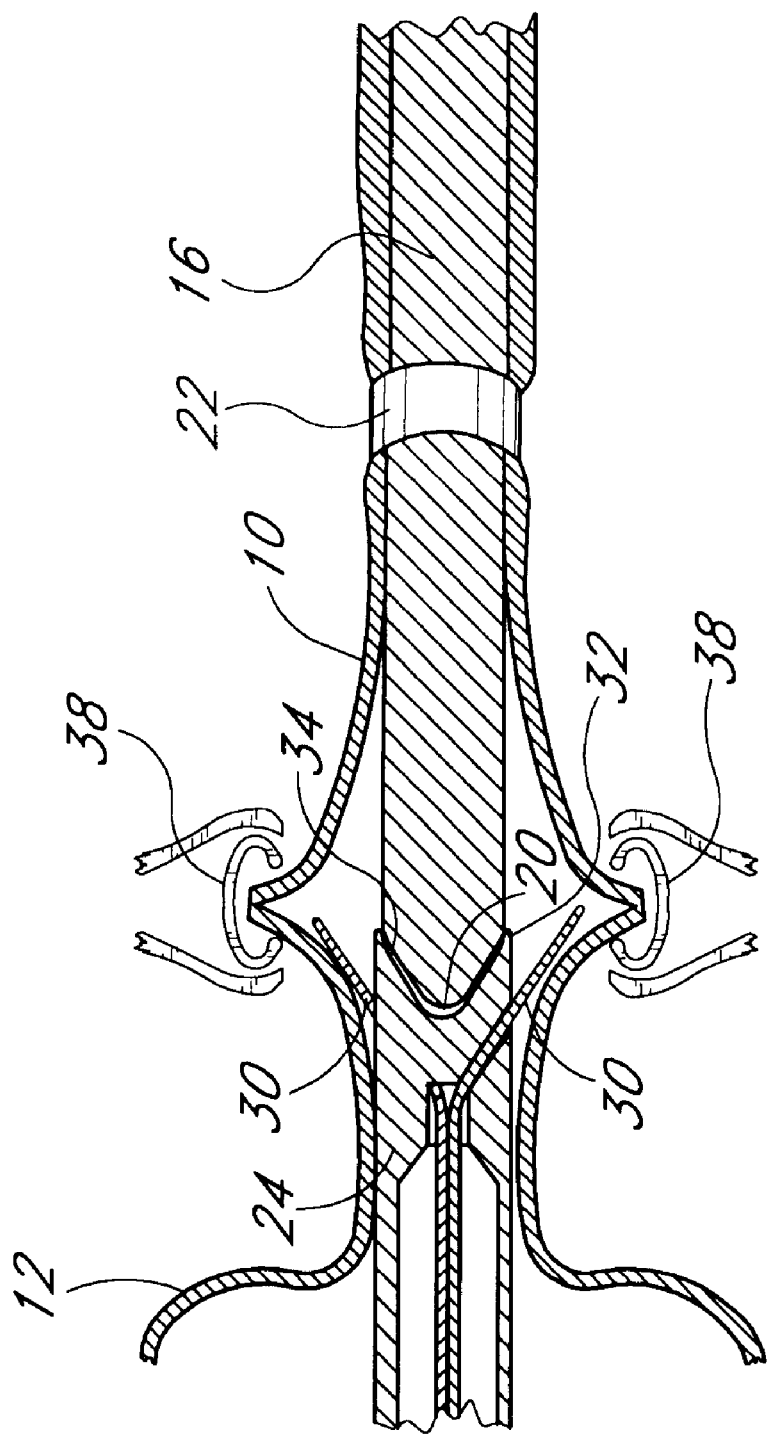
FIG. 2 is a cross-sectional view of the trocar and sheath, and the juncture of the bladder and urethra.
Figure 5:
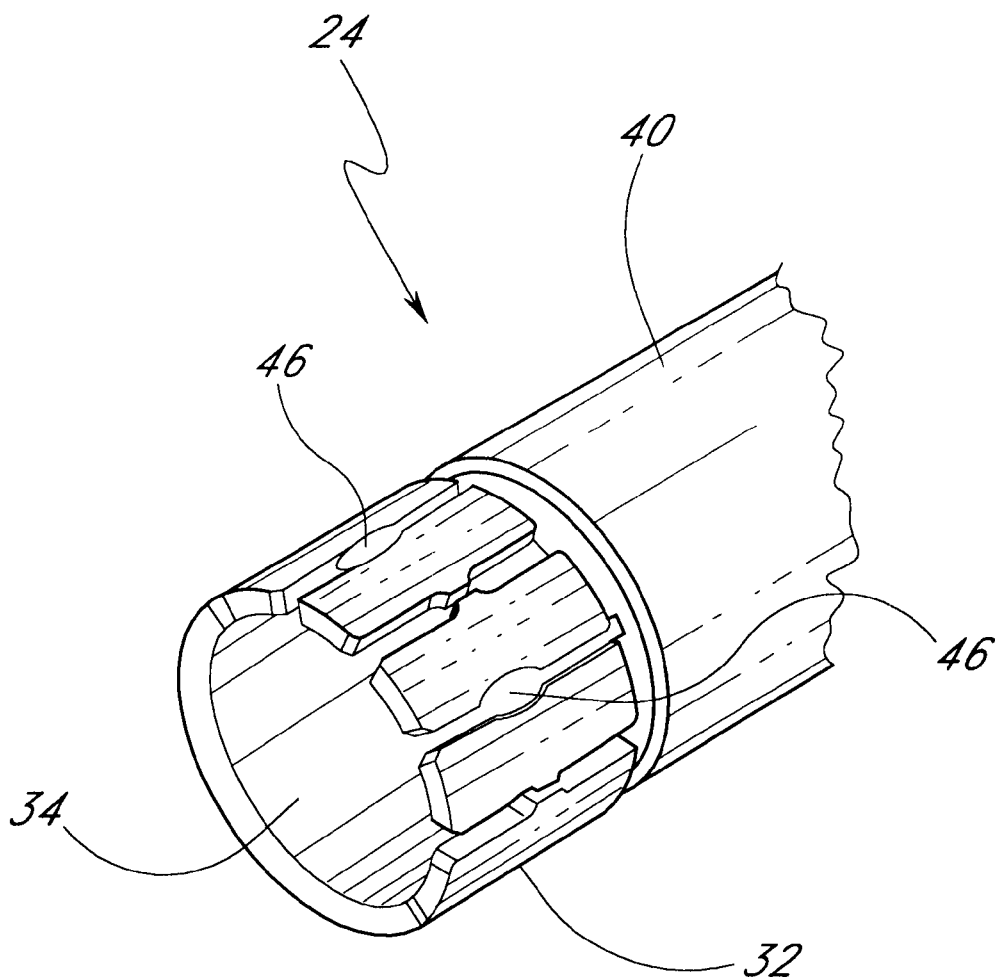
FIG. 5 is a close-up perspective view of the distal end of a sheath.

With further reference now to FIG. 2, the surgeon advances the sheath 24 toward the trocar 16, stretching the bladder 12 in the process. In one embodiment, the surgeon also moves the trocar 16 toward the sheath 24, stretching the urethra 10 in the process. When the trocar 16 and the sheath 24 meet, the tapered distal end 20 of the trocar 16 enters the cavity 34 in the distal end 32 of the sheath 24, to an extent sufficient to enable the urethral tissue and the bladder tissue to press together as shown. Fit together in this manner, the trocar 16 and the sheath 24 can retain the tissues in this orientation suitable for the connection process, in a "hands-free" manner. The tissues of the urethra 10 and the bladder 12 are subsequently clamped together using one or more external clips 38, around the circumference of the urethra-bladder attachment. The application of the clips may effect disengagement of the bladder tissue 12 from the everting prongs 30. In one embodiment, VCS clips are used to secure the urethral tissue to the bladder. The clips 38 may be applied either individually, or simultaneously in a "one-shot" fashion.

After the application of the clips 38, the external ring 22 is removed, releasing the trocar 16 from the urethra 10. The surgeon is now able to remove the trocar 16 via the urethral outlet in a manner known to those skilled in the art. Similarly, the sheath 24 may be moved in the proximal direction, after retracting the everting prongs 30 by manipulation of the everting knob 26. The sheath 24 exits the bladder 12 through the incision 36.

Figure 6:
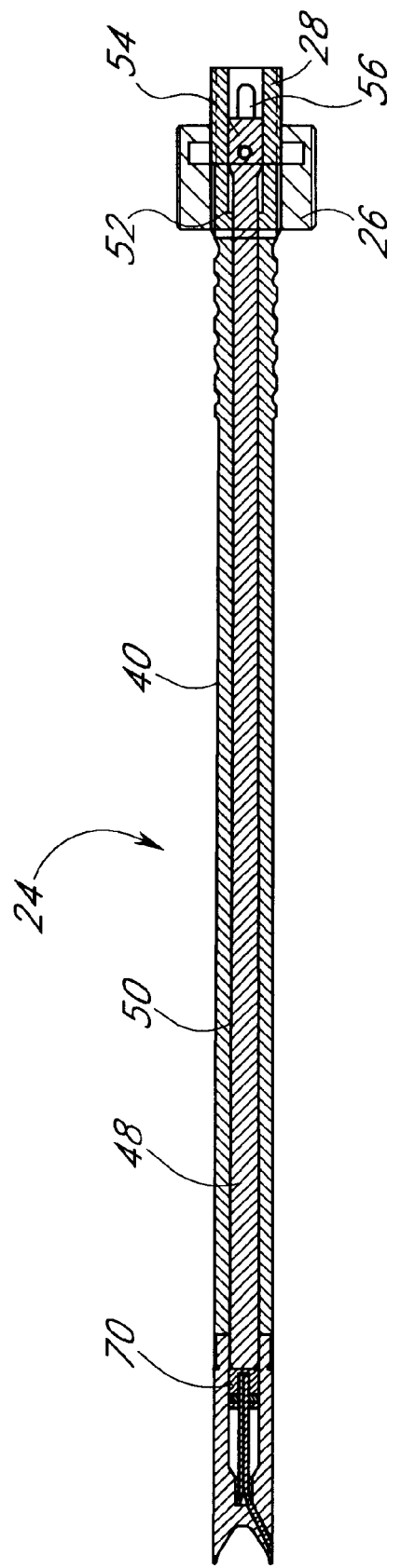
FIG. 6 is a side cross-sectional view of a sheath.

FIGS. 3–9 show the components of the sheath 24 in detail. The sheath 24 has an elongated cannula 40 with a cavity 34 in the distal end 32 and an everting knob 26 near the proximal end 28. FIGS. 3, 4 and 6 show a sheath 24 which is straight; advantageously, the sheath may be curved as seen in FIG. 1, to promote ease of insertion and use. (Similarly, the straight instruments seen in FIGS. 10, 12, 13 and 14 may also be curved, to obtain the same advantages.) The everting knob 26 engages threads 42 near the proximal end of the sheath so that rotating the everting knob 26 causes it to advance in the desired direction (either distally or proximally) along the threaded portion of the sheath 24. Knurling 44 is provided on both the cannula surface and the everting knob to facilitate easy gripping of the knob and sheath during surgery. Best shown in FIG. 5, a number (preferably 4–6) of openings 46 are distributed radially about the circumference of the cannula 40, near the distal end 32. The openings 46 permit everting prongs (not shown)

to extend from, or retract into, the cannula 40 when the everting knob 26 is rotated.

As seen in FIG. 6, an everting tube 48 is disposed within a lumen 50 of the cannula 40 and is coaxial with the cannula 40. The everting tube 48 fits snugly within the lumen 50 but can easily move longitudinally within the cannula 40 in both the distal and proximal directions. Near its proximal end the lumen 50 widens at a neck 52 to take on a larger-diameter cross section proximal of the neck 52. Correspondingly, the everting tube 48 widens to form a stub 54 disposed within the larger-diameter portion of the lumen 50. The neck 52 coacts with the stub 54 to limit the travel of the everting tube 48 in the distal direction.

Figure 7:
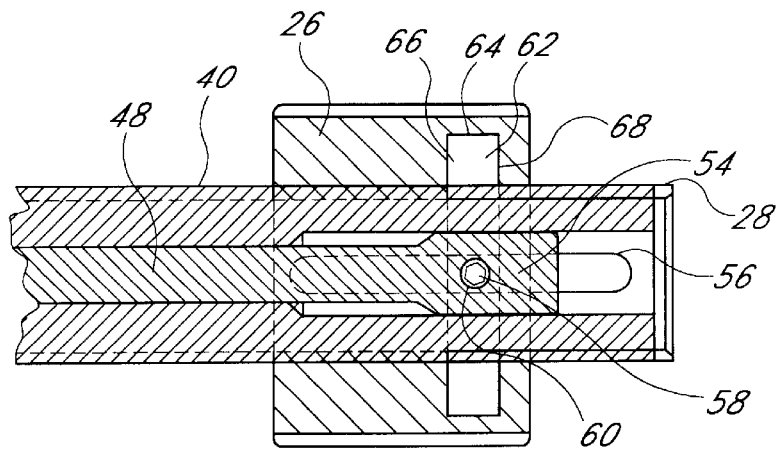
FIG. 7 is a detail cross-section view of the proximal end of a sheath.
Figure 8:
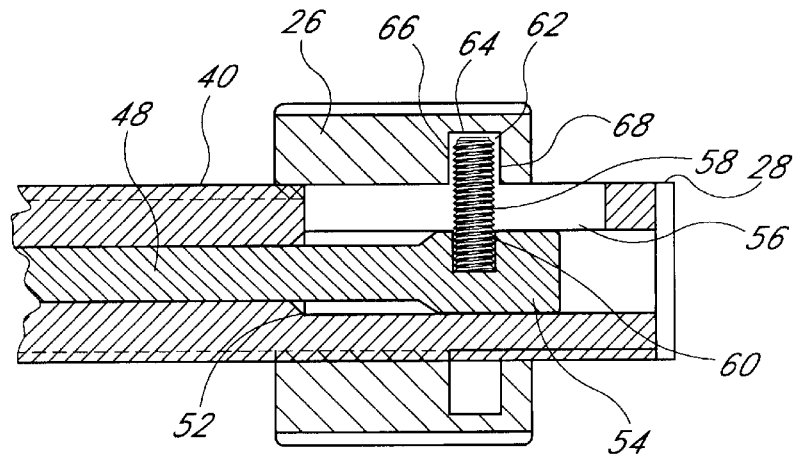
FIG. 8 is a second detail cross-section view of the proximal end of a sheath, oriented 90° to the view in FIG. 7.
Figure 9:
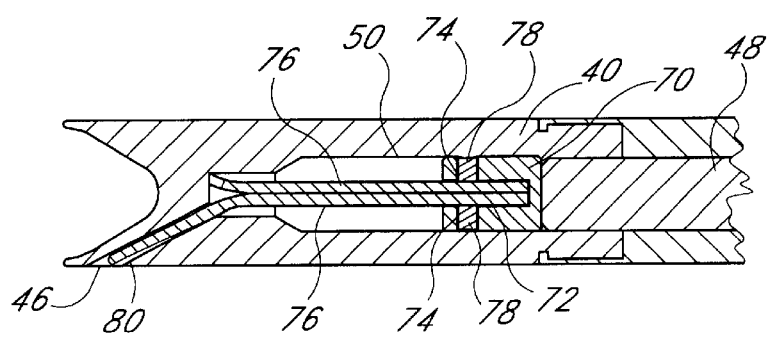
FIG. 9 is a detail cross-section view of the distal end of a sheath.

FIGS. 7 and 8 show the proximal end 28 of the sheath 24 in detail. Note that FIGS. 7 and 8 are oriented 90° with respect to one another, so that FIG. 7 may be considered a side view and FIG. 8 a top view. A longitudinal slot 56 is formed in the wall of the cannula 40 near the proximal end 28. The slot 56 permits an allen screw 58 to extend from a threaded hole 60 in the stub 54 beyond the external wall of the cannula 40 and into a space 62 formed by a radial groove 64 in the everting knob 26, between distal and proximal walls 66, 68.

With the screw 58 in place, one can cause the everting tube 48 to move in either the distal or proximal direction by manipulating the everting knob 26. If the everting knob 26 is rotated so as to advance in the distal direction, the proximal wall 68 of the radial groove 64 bears on the screw 58 as the everting knob advances distally, causing the everting tube 48 to move distally within the lumen 50. Similarly, if the everting knob 26 is rotated so as to advance in the proximal direction, the distal wall 66 of the radial groove 64 will bear on the screw 58, causing the everting tube 48 to move proximally within the lumen 50.

Referring momentarily to FIG. 6, it can be seen that the distal end of the everting tube 48 is connected to a bushing 70, which is disposed within the lumen 50 and is moveable both distally and proximally therein. Best seen in FIG. 9, the bushing 70 forms a longitudinal socket 72 and two threaded holes 74 intersecting the socket 72. The socket 72 receives the proximal ends of a number of everting wires 76, and screws 78 threaded into the holes 74 clamp the everting wires 76 into the bushing 70.

The everting wires 76 extend distally from the bushing 70 into angled channels 80 that correspond to the openings 46 in the distal end of the cannula 40. The angled channels 80 force the distal ends of the everting wires, when moved distally, to extend from the cannula so as to form everting prongs 30 (see FIG. 2). Similarly, the everting wires 76 retract into the angled channels 80 when moved proximally.

Thus it can be seen that rotation of the everting knob 26 in the desired direction will extend or retract the everting prongs 30. When the everting knob 26 is rotated in a direction causing the everting tube 48 to move distally, the everting tube 48 pushes the bushing 70 in the distal direction, forcing the everting wires 76 to extend from the openings 46 and form everting prongs. By rotating the everting knob 26 in the opposite direction, the everting tube 48 moves proximally and pulls the bushing 70 proximally as well, causing the everting wires 76 to retract into the angled channels 80.

Figure 10:
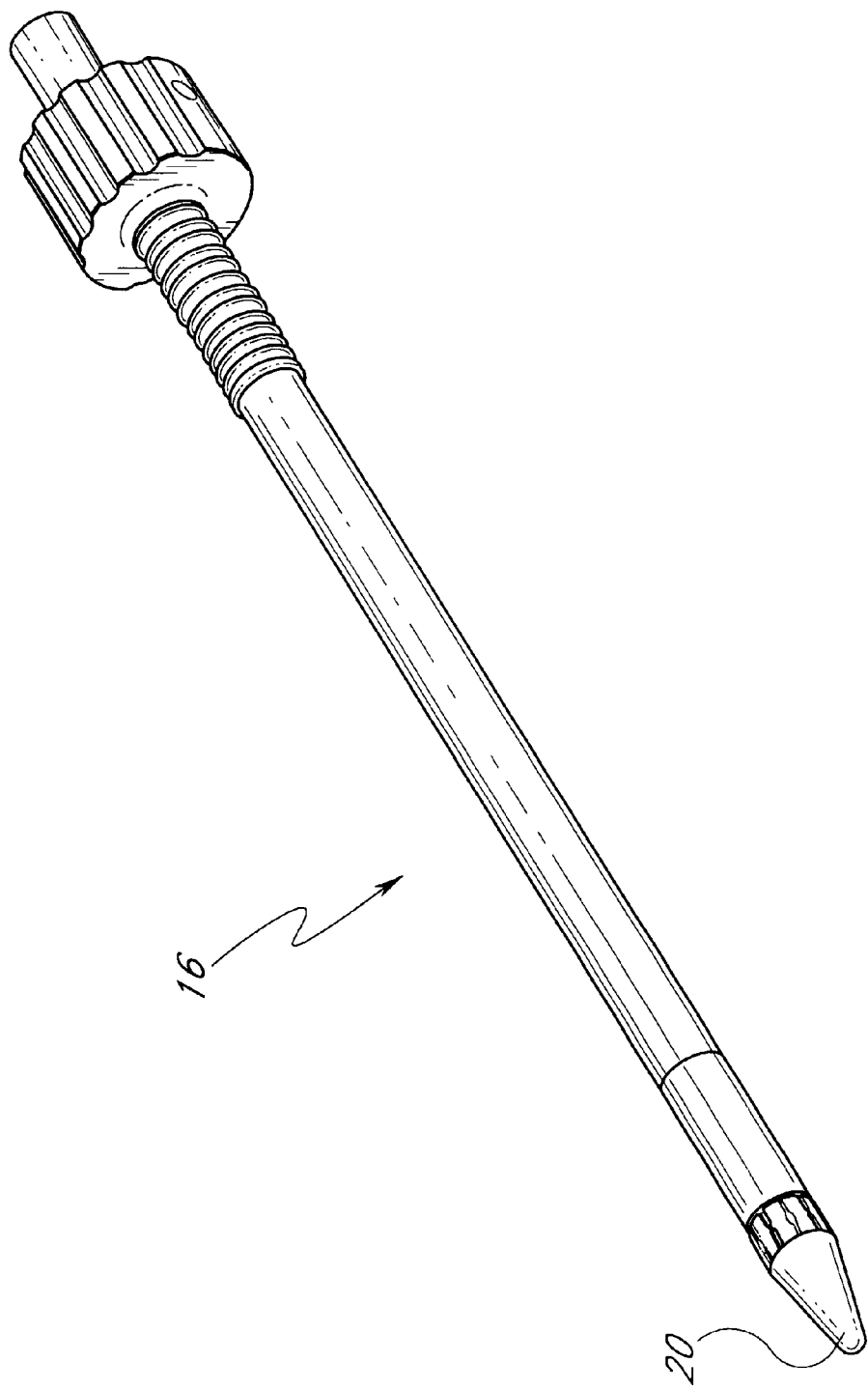
FIG. 10 is a perspective view of another embodiment of a trocar in accordance with the invention.

FIG. 10 shows an alternative embodiment of the trocar 16, which employs the same everting-prong mechanism as the sheath discussed above. This type of trocar also has a tapered distal tip 20 which fits snugly into the cavity formed in the distal end of the sheath.

FIG. 11A depicts the use of the everting-prong mechanism of the sheath 24 with the bladder tissue 12. Additionally, FIG. 11A shows the use of that version of the trocar 16 employing a similar mechanism, with the urethra 10. After positioning the distal end 32 of the sheath 24 near the bladder outlet 14, the surgeon extends the everting prongs 30, which engage the bladder tissue 12, everting the bladder outlet 14 and holding it in a suitable position for attachment to the urethra 10. When using a trocar 16 equipped with everting prongs 30, the surgeon inserts the trocar 16 into the urethra 10 and positions the distal end 20 near the opening of the urethra 10. In a similar manner the everting prongs 30 are extended so as to evert the tissue near the end of the urethra 10 in the desired position for reattachment.

After everting both the bladder and urethra tissue, the surgeon brings the trocar 16 and sheath 24 together so that the tapered distal end 20 of the trocar 16 fits into the cavity 34 of the sheath, and the bladder and urethra tissue meet. Upon joining the trocar and sheath, the surgeon has both hands free to perform final alignment of the bladder and urethra tissue, and apply the clips 38 as shown in FIG. 11B.

Figure 12:
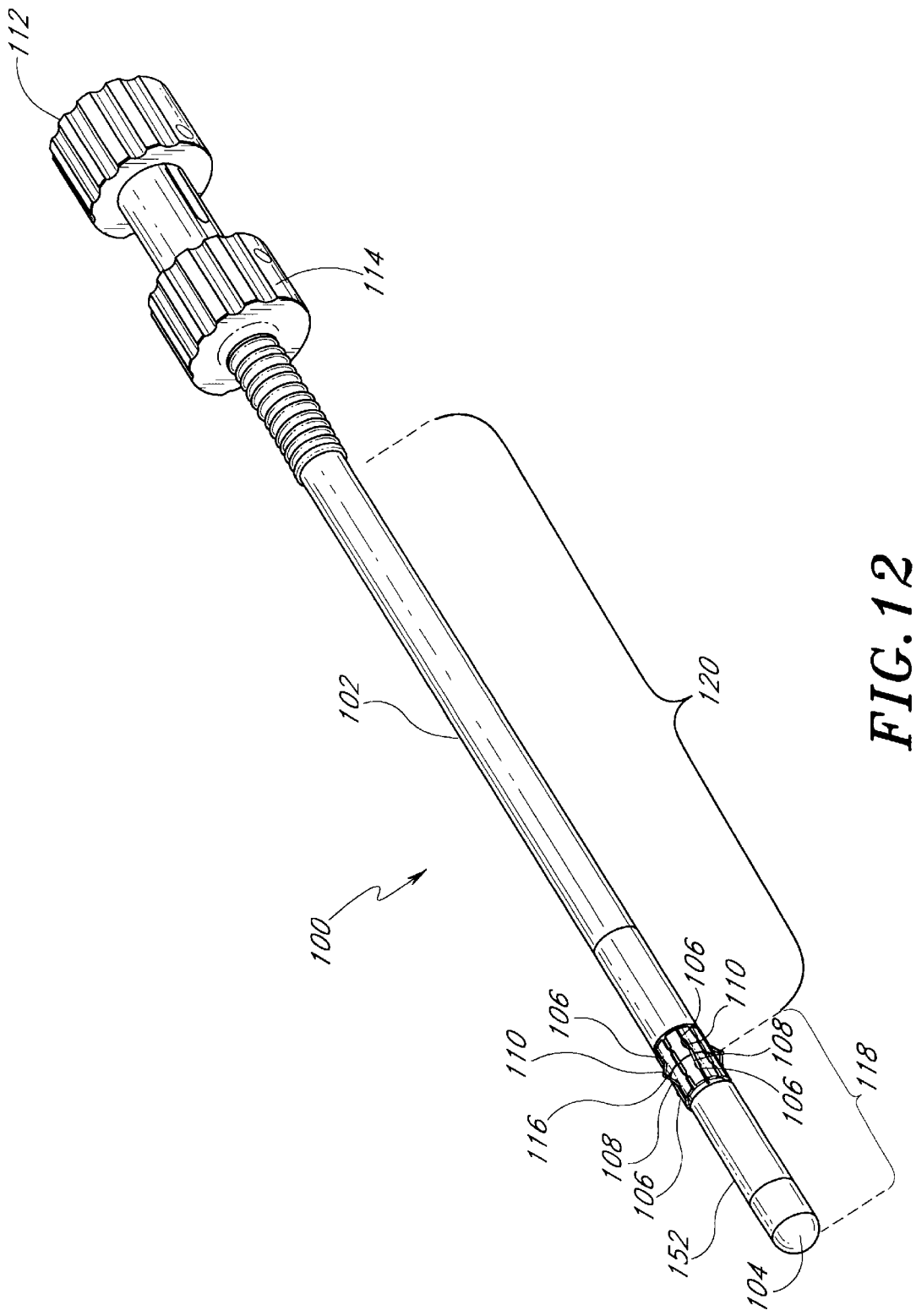
FIG. 12 is a perspective view of a dual approximator.
Figure 13:
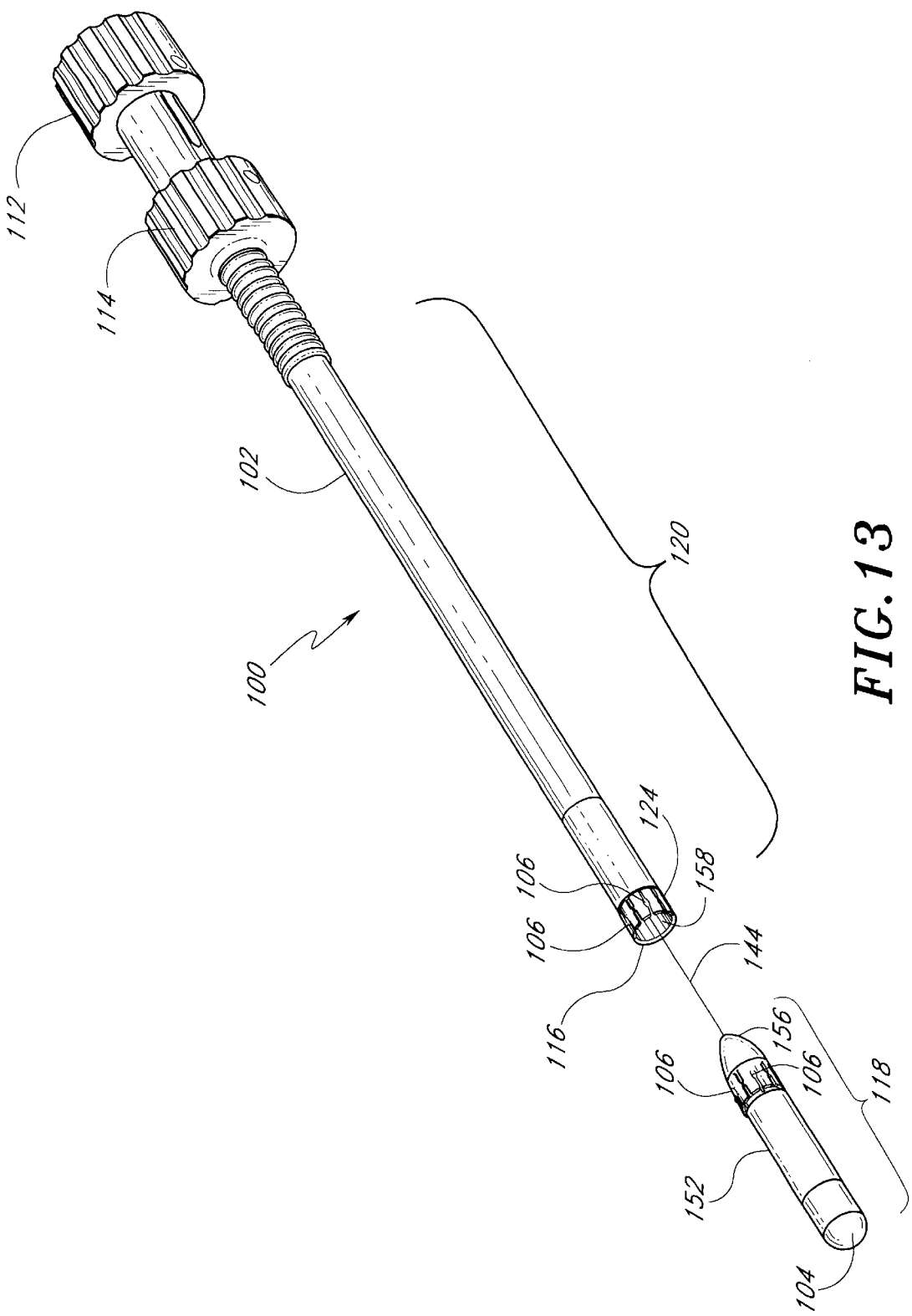
FIG. 13 is a perspective view of a dual approximator, with the bladder everting device displaced in the distal direction.
Figure 14:
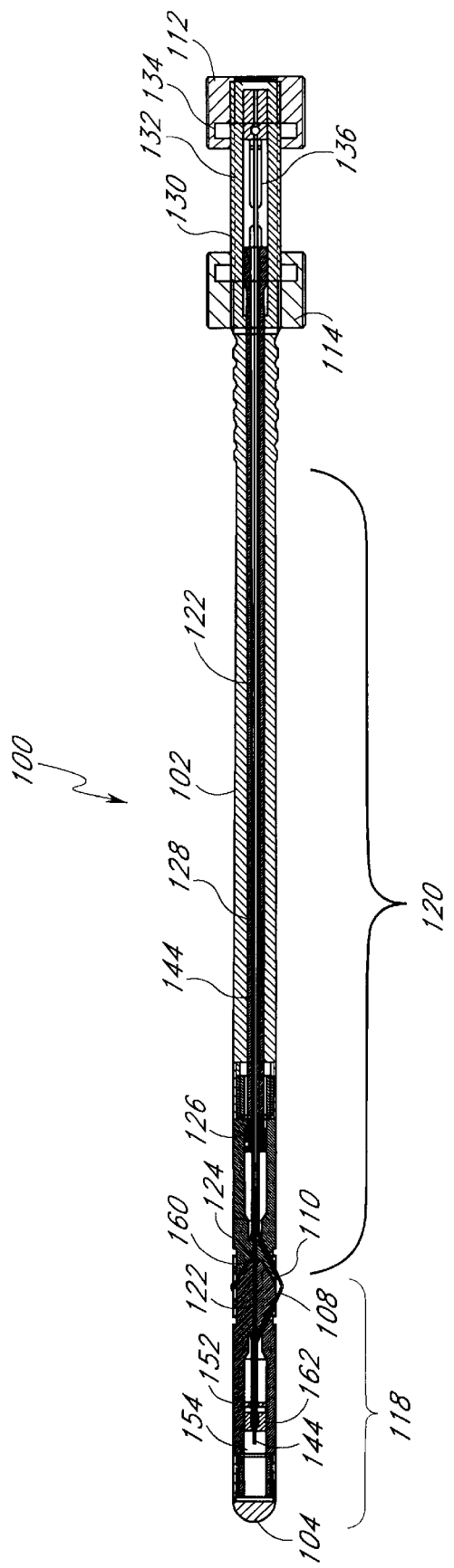
FIG. 14 is a cross-sectional view of a dual approximator.

FIGS. 12–14 show yet another embodiment of the instruments to be used in the present invention. This embodiment enables a surgeon to perform the operation without making an incision in the bladder (otherwise needed to insert the sheath) by combining the functions of the trocar and the sheath in a dual approximator 100 to be used transurethrally.

The dual approximator 100 has an elongated cannula 102 with a rounded distal end 104, two sets of openings 106 in the surface of the cannula 102 for the bladder and urethra everting prongs 108, 110, and a bladder everting knob 112 and a urethra everting knob 114 near the proximal end. As seen in FIG. 13, The cannula 102 is separable at a point 116 between the two sets of openings 106, into a bladder everting unit 118 and a urethra everting unit 120. This separation feature permits the bladder everting unit 118 to move distally, into the bladder opening as necessary. Preferably, the bladder and urethra everting prongs 108, 110 are radially staggered with respect to one another so that the two sets of prongs will not "collide" when extended.

Figure 15:
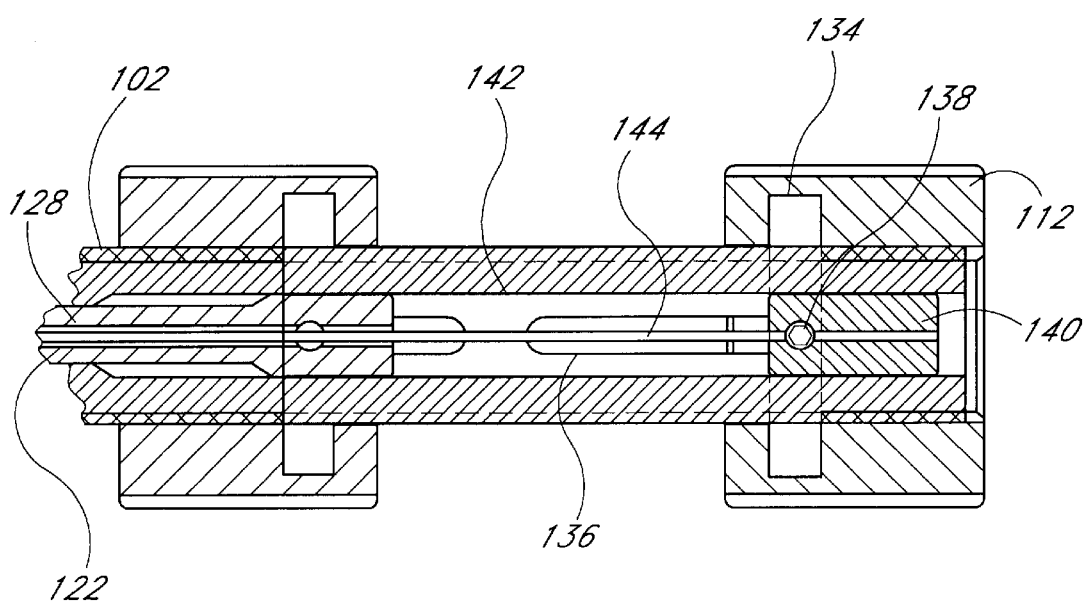
FIG. 15 is a detail cross-sectional view of the proximal end of a dual approximator.
Figure 16A:
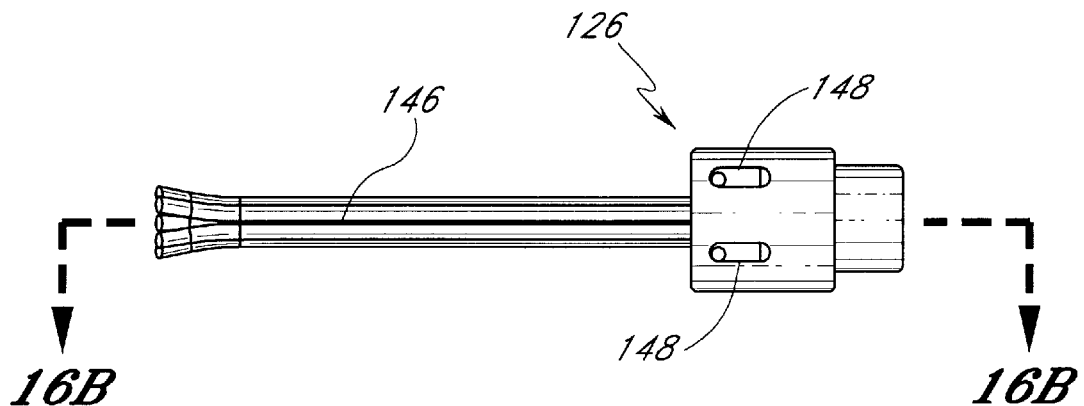
FIGS. 16A–16C are side elevation, side cross-section, and perspective views of a bushing and everting wire assembly for use with a dual approximator.
Figure 16B:
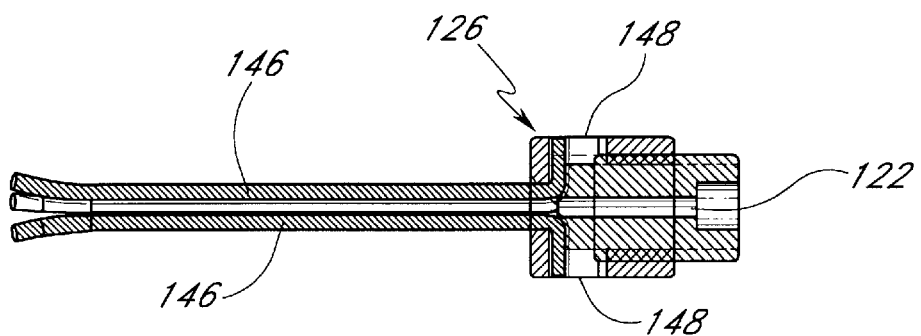
Figure 16C:
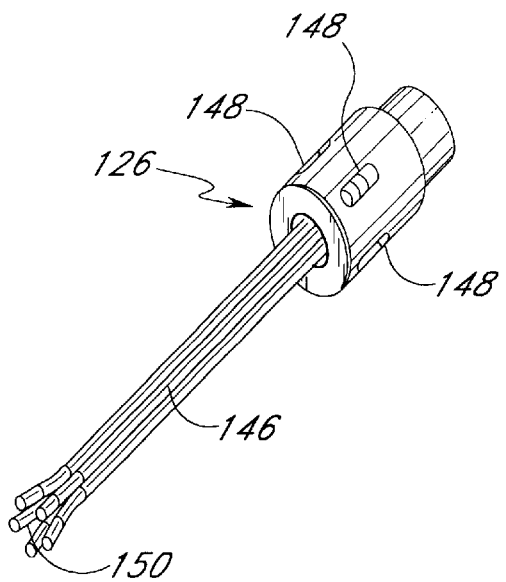

The urethra everting unit 120 resembles the sheath described above, with some additions best seen in FIG. 14. A central channel 122 runs along the centerline of the urethra everting unit 120, through the distal end 124, bushing 126, everting tube 128 and stub 130. A bladder everting knob 112 is located proximal of a urethra everting knob 114, and engages threads on the outer surface of the cannula 102 so that rotation of the bladder everting knob 112 causes it to advance in the desired direction (either distally or proximally) along the threaded portion of the cannula 102. Best seen in FIG. 15, a radial channel 134, longitudinal slot 136, screw 138, and block 140 coact in a manner similar to that disclosed above with respect to the everting knob 26 on the sheath 24, to cause the block 140 to move longitudinally within the lumen 142 of the cannula 102 in response to rotation of the bladder everting knob 112 in the desired direction.

Attached to the block 140 is a bladder everting rod 144 which runs through the central channel 122 and out the distal end 124, continuing into the bladder everting unit 118 (see FIG. 14). To accommodate the central channel 122 and bladder everting rod 144, the bushing 126 is modified as shown in FIGS. 16A–16C, and 17. Urethra everting wires 146 are bent 90° at the proximal ends and are received in slots 148 formed at the distal end of the bushing 126. The central channel 122 and the bladder everting rod 144 (best seen in FIG. 17) pass through the bushing 126, and the bladder everting rod 144 continues distally through a space 150 formed between the urethra everting wires 146. This arrangement of the bushing 126 and urethra everting wires 146 permits the bladder everting rod 144 and urethra everting wires 146 to move freely with respect to each other within the cannula 102 without interference.

Figure 17:
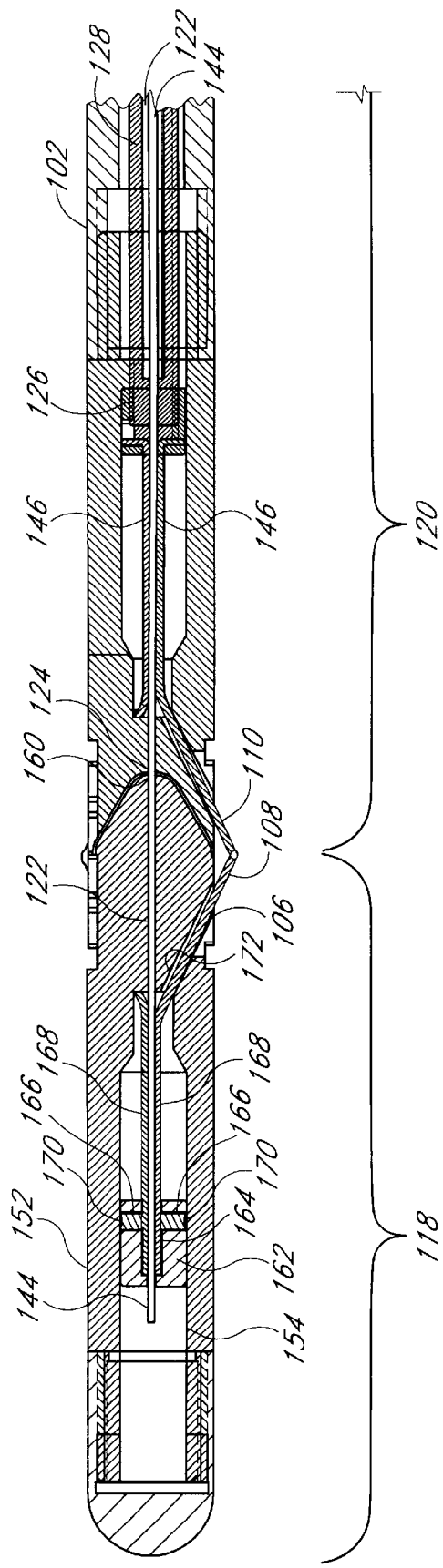
FIG. 17 is a detail cross-sectional view of the distal end of a dual approximator.

Referring again to FIGS. 12–14, the bladder everting unit 118 is located at the distal end of the dual approximator 100, and has a relatively short cannula 152 with a lumen 154 and a rounded distal tip 104. The proximal end 156 is tapered, in the same way as the distal end of the trocar 16, to fit within the cavity 158 formed in the distal end 124 of the urethra everting unit 120. Near the proximal end 156 are located a number (preferably 4–6) of openings 106 distributed radially about the circumference of the cannula 152. As seen in FIG. 17, the central channel 122 continues from an opening 160 in the proximal tip, along the longitudinal axis of the bladder everting unit 118, to the proximal end of the lumen 154.

A bushing 162 is disposed within the lumen 154 and is moveable both distally and proximally therein. The bladder everting rod 144 passes through the central channel 122, into the lumen 154, and to the bushing 162. The bushing 162 forms a longitudinal socket 164 and two threaded holes 166 which intersect with the socket 164. The socket 164 receives the distal ends of a number of bladder everting wires 168 and the bladder everting rod 144, and screws 170 threaded into the holes 166 clamp the wires 168 and rod 144 into the bushing 162.

The bladder everting wires 168 extend proximally from the bushing 162 into angled channels 172 corresponding to the openings 106 in the proximal end of the bladder everting unit 118. The angled channels 172 force the proximal ends of the everting wires 168, when moved proximally, to extend from the cannula 152 so as to form everting prongs 108. Similarly, the bladder everting wires 168 will retract into the angled channels 172 when moved distally.

Thus, by reference especially to FIGS. 14 and 17, it can be seen that rotation of the bladder everting knob 112 in the desired direction will extend or retract the bladder everting prongs 108. When the bladder everting knob 112 is rotated in a direction causing the bladder everting rod 144 to move proximally, the bladder everting rod 144 will pull the bushing 162 in the proximal direction, forcing the bladder everting wires 168 to extend from the openings 106 and form bladder everting prongs 108. By rotating the bladder everting knob 112 in the opposite direction, the bladder everting rod 144 moves distally and pushes the bushing 162 distally as well, causing the bladder everting wires 168 to retract into the angled channels 172.

The bladder everting knob 112 also expands or contracts the distance between the urethra everting unit 120 and the bladder everting unit 118. When the bushing 162 in the bladder everting unit 118 remains relatively immobile, rotation of the bladder everting knob 112 so as to move the bladder everting rod 144 distally or proximally, causes a corresponding distal or proximal movement of the bladder everting unit 118.

Figure 18:
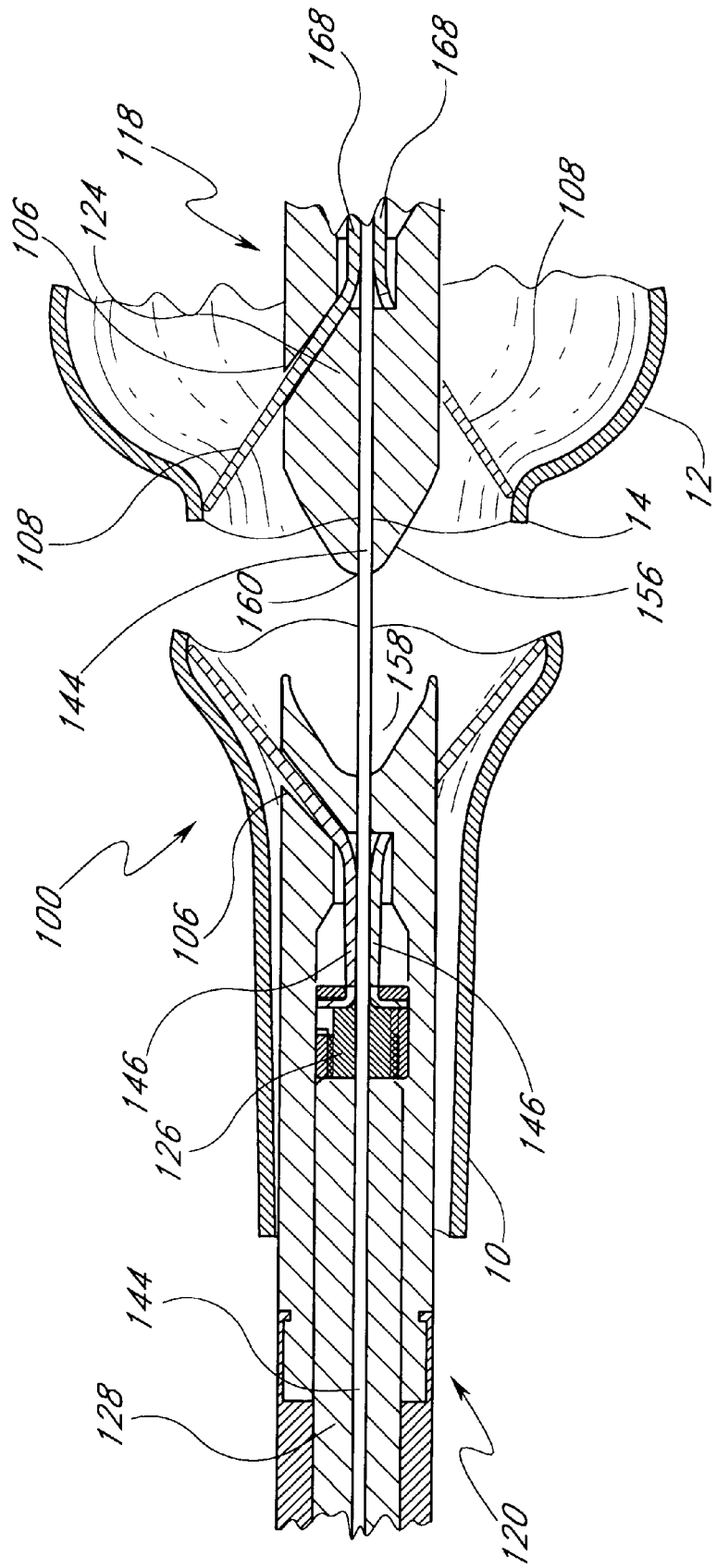
FIG. 18 is a cross-sectional view of the use of the dual approximator to join the bladder to the urethra.

FIG. 18 details the use of the dual approximator 100 in performing the anastomosis procedure. The surgeon inserts the dual approximator 100 into the lumen of the urethra 10, through the urethral outlet, in a manner known to those skilled in the art. The dual approximator 100 is advanced within the lumen of the urethra 10 until the distal end of the dual approximator 100, including the bladder everting unit 118, emerges from the opening. Next the surgeon rotates the bladder everting knob so as to move the bladder everting unit 118 distally and create a suitable gap between the bladder everting unit 118 and the urethra everting unit 120. The bladder everting unit 118 is then inserted into the bladder opening 14, to a point where the openings 106 in the bladder everting unit 118 are properly aligned within the bladder 12. The surgeon then rotates the bladder everting knob to extend the bladder everting wires 168 from the openings 106, forming everting prongs 108, until the tips of the prongs 108 contact and evert the bladder tissue 12. Similarly, the surgeon rotates the urethra everting knob to evert the end of the urethra 10 as desired. The surgeon then brings the everted bladder and urethra tissue 12, 10 together by further rotating the bladder everting knob until the tapered proximal end 156 of the bladder everting unit 118 meets the cavity 158 in the distal end of the urethra everting unit 120. At this point the surgeon will have both hands free to perform final alignment of the bladder and urethra tissue 12, 10, and apply the clips 38 in a similar manner as shown in FIG. 11B. After applying the clips 38, the surgeon rotates the bladder everting knob to retract both sets of everting wires, and then withdraws the dual approximator 100 from the urethra 10.

The clips 38 perform a holding function, in a manner similar to sutures but without penetration of the vessel walls. One example of a suitable clip for use in this procedure is disclosed in U.S. Pat. No. 4,983,176, titled DEFORMABLE PLASTIC SURGICAL CLIP, the entirety of which is hereby incorporated herein by reference.

The present invention utilizes a simple, effective mechanical arrangement for reconnecting the bladder to the urethra. By eliminating the painstaking, cumbersome suturing techniques, urethral-vascular anastomosis techniques are improved. Furthermore, in the disclosed procedure, there is provided improved apparatus for grasping and everting the urethra and bladder tissues, leaving the surgeon's hands free for performing the reconnection step of the anastomosis process.

By utilizing the disclosed techniques and apparatus, the number of steps in the anastomosis procedure is decreased, minimizing cost and reducing the required time for the procedure. The present invention eliminates many complications associated with other anastomosis techniques, such as stapling or suturing. Because the clips do not penetrate the vessel walls, there is a decreased likelihood of clotting, which may cause stricture. The clips also reduce the occurrence of necrosis, which occurs when insufficient blood is supplied to the joined tissues. In addition, the use of clips eliminates the possibility of piercing the neurovascular bundle with the suture needle(s), which piercing can cause impotence and/or incontinence.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A system for securing the urethra of a patient to the bladder of the patient, the system comprising:
   a first elongated member adapted to be inserted into the urethra of the patient, the first elongated member having a first mating end;

a second elongated member adapted to be inserted into the bladder of the patient, the second elongated member having a second mating end;

wherein the first mating end and the second mating end are adapted to receive one another so as to place the first elongated member and the second elongated member in end-to-end fitting engagement; and at least one clip, the clip being suitable to secure the urethra and the bladder once the urethra and bladder are within close proximity.

2. The system of claim 1 further comprising a ring, the ring being suitable for placement on an exterior of the urethra for securing the urethra to the first elongated member.

3. The system of claim 1 wherein the at least one clip comprises at least one VCS clip.

4. The system of claim 1 wherein the at least one clip comprises opposing grip portions which are configured to grip the bladder and urethra in a non-penetrating fashion.

* * * * *